US006168782B1

(12) United States Patent
Lin et al.

(10) Patent No.: US 6,168,782 B1
(45) Date of Patent: Jan. 2, 2001

(54) ELASTOMERIC SILICONE CONTAINING AN ACTIVE INGREDIENT

(75) Inventors: Zuchen Lin; William James Schulz, Jr., both of Midland; Janet Mary Smith, Bay City, all of MI (US)

(73) Assignee: Dow Corning Corporation, Midland, MI (US)

( * ) Notice: Under 35 U.S.C. 154(b), the term of this patent shall be extended for 0 days.

(21) Appl. No.: 09/317,459

(22) Filed: May 24, 1999

(51) Int. Cl.$^7$ .......................... A61K 31/74; A61K 7/32; A61L 9/00; C08L 83/04; C08G 77/06

(52) U.S. Cl. .................. 424/78.03; 424/65; 424/70.1; 424/76.1; 424/401; 523/102; 523/103; 523/105; 523/122; 524/231; 524/709; 524/714; 524/722; 524/725; 524/726; 524/751; 524/754; 524/755; 524/759; 524/762; 524/765; 524/770; 524/773; 524/774; 524/792; 524/837; 524/861; 524/862; 528/15; 528/25

(58) Field of Search .................. 424/78.03, 65, 424/70.1, 76.1, 401; 524/709, 714, 722, 725, 726, 751, 754, 755, 759, 762, 765, 770, 773, 774, 792, 231, 837, 861, 862; 528/15, 25; 523/102, 103, 105, 122

(56) References Cited

U.S. PATENT DOCUMENTS

| | | | |
|---|---|---|---|
| 5,401,870 | * 3/1995 | Raleigh et al. | 556/445 |
| 5,472,686 | * 12/1995 | Tsubaki et al. | 424/59 |
| 5,654,362 | 8/1997 | Schulz | 524/862 |
| 5,660,819 | * 8/1997 | Tsubaki et al. | 424/70.1 |
| 5,811,487 | 9/1998 | Schulz | 524/862 |
| 5,880,210 | 3/1999 | Schulz | 524/731 |
| 5,889,108 | 3/1999 | Zhang | 524/862 |
| 5,948,855 | * 9/1999 | Lin et al. | 524/837 |
| 5,969,035 | * 10/1999 | Meinhardt et al. | 524/731 |

* cited by examiner

*Primary Examiner*—Robert Dawson
*Assistant Examiner*—Jeffrey B. Robertson
(74) *Attorney, Agent, or Firm*—James L. De Cesare

(57) ABSTRACT

Elastomeric silicones, especially elastomeric silicone polyethers, are prepared by combining and reacting (A) an $\equiv$Si—H containing polysiloxane, (B) a mono-alkenyl polyether, (C) an active ingredient such as a vitamin, antimicrobial agent, sunburn prevention agent, astringent, or sex hormone, (D) an $\alpha,\omega$-unsaturated hydrocarbon, (E) a platinum catalyst, and (F) an oil. The reaction of components (A)–(F) is allowed to continue, forming a crosslinked three-dimensional gelled network of the elastomeric silicone polyether containing the active ingredient and the oil. The compositions are useful in personal and health care applications, personal hygiene, and household cleaning applications.

11 Claims, No Drawings

ELASTOMERIC SILICONE CONTAINING AN ACTIVE INGREDIENT

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to crosslinked three-dimensional gelled networks of elastomeric silicones, especially elastomeric silicone polyethers, containing an active ingredient and an oil. The compositions can be used in personal and health care applications, personal hygiene, and household cleaning applications.

BACKGROUND OF THE INVENTION

While U.S. Pat. No. 5,811,487 (Sep. 22, 1998) and U.S. Pat. No. 5,889,108 (Mar. 30, 1999), each teach processes for making elastomeric silicone polyethers containing oils and solvents, neither patent describes a process in which an elastomeric silicone polyether is made in the presence of an active ingredient as defined herein.

Thus, neither patent teaches the inclusion of an active ingredient such as a vitamin, antimicrobial agent, sunburn prevention agent, astringent, or hormone, for example, during the gelation stage, i.e., the crosslinking step, of the reaction.

This is significant because it now enables one to successfully entrap an active ingredient into the silicone gel matrix of such elastomeric silicone polyethers. Unexpectedly, a structural determination by $^{29}$Si nuclear magnetic resonance (NMR) revealed actual chemical bonding of some active ingredients, i.e., vitamin E, to the silicone gel matrix of the elastomeric silicone polyether. This is both beneficial and an advantage, as it now provides an avenue for entrapping vitamins, and other types of active ingredients, in cosmetics, personal care products, and pharmaceuticals; and for controlling their release in various types of delivery systems.

Thus, it will be demonstrated herein that elastomeric silicone polyethers can be made in the presence of active ingredients such as vitamin E. For example, vitamin E was added during the crosslinking step of the reaction. The reaction produced a clear gel with a golden tint, containing about 15% by weight of the elastomeric silicone polyether. Upon further dilution of the gel, it was found that the final product remained clear and had a golden tint. The vitamin was noted to be stable and entrapped in the gel. Other active ingredients such as antimicrobial agent 5-chloro-2-(2,4-dichlorophenoxy)phenol, i.e., TRICLOSAN; sunburn prevention agent 2-ethylhexyl methoxy cinnamate, i.e., OCTYLMETHOXY CINNAMATE; astringents aluminum chlorohydrate and aluminum zirconium tetrachlorohydrex glycine complex; and estradiol, a female sex hormone; were also successfully entrapped in these gel matrices of elastomeric silicone polyether.

BRIEF SUMMARY OF THE INVENTION

This invention relates to a composition which is an elastomeric silicone, especially an elastomeric silicone polyether containing an active ingredient, prepared by reacting (A) an $\equiv$Si—H containing polysiloxane and (B) a mono-alkenyl polyether in the presence of a platinum catalyst, until (C) an $\equiv$Si—H containing polysiloxane with polyether groups is formed; and reacting (C) the $\equiv$Si—H containing polysiloxane with polyether groups and (D) an $\alpha,\omega$-unsaturated hydrocarbon such as an $\alpha,\omega$-diene, $\alpha,\omega$-diyne, or an $\alpha,\omega$-ene-yne, in the presence of (E) an active ingredient, (F) an oil, and a platinum catalyst, until a silicone elastomer is formed by crosslinking and addition of $\equiv$SiH across double or triple bonds in the $\alpha,\omega$-unsaturated hydrocarbon. The reaction is allowed to continue until there is formed a crosslinked three-dimensional gelled network of an elastomeric silicone polyether containing the active ingredient and the oil. The composition can be prepared using an oil-soluble as well as a water-soluble active ingredient.

It should be clearly understood, that within the context of this invention, the phrase active ingredient and the term "oil" are not synonymous. Thus, the active ingredient is not the "oil", and the "oil" is not the active ingredient.

The invention further relates to emulsions and multiple emulsions containing the composition.

In this regard, it is noted that multiple emulsions are composed of droplets of one liquid dispersed in larger droplets of a second liquid which are then dispersed in a final continuous phase. Generally, the internal droplet phase will be miscible with or identical to the final continuous phase. For example, in a water-in-oil-in-water multiple emulsion W/O/W, the internal and external phases are aqueous.

For a W/O/W system, in which the final continuous phase is aqueous, the primary emulsion is a water-in-oil emulsion W/O, which is then emulsified into the final aqueous phase.

For the purpose of clarity, and according to recognized standards of nomenclature used for W/O/W systems, the aqueous phase of the primary emulsion is designated as $W_1$, and the primary emulsion is designated as $W_1/O$. The primary emulsion $W_1/O$ includes an oil phase which is designated as O. After the primary emulsion $W_1/O$ has been further dispersed in the second aqueous phase designated as $W_2$, the complete multiple emulsion system is designated as $W_1/O/W_2$.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

According to this invention, an elastomeric silicone, especially an elastomeric silicone polyether containing an active ingredient, can be prepared and used as generally depicted in one or more of the several processing steps shown below:

Step 1: Incorporation of the Polyether $\equiv$SiH siloxane+mono-alkenyl polyether+Pt catalyst$\rightarrow$$\equiv$SiH siloxane with polyether groups Step 2: Gelation $\equiv$SiH siloxane with polyether groups+active ingredient+oil+$\equiv$SiH siloxane (optional)+$\alpha,\omega$-unsaturated hydrocarbon $$\text{gel/elastomer} \xrightarrow{Pt}$$

Step 3: Shearing & Swelling—Optional
   gel/elastomer+additional oil+additional active ingredient+quencher→paste Step 4: Emulsification/Preparation of Primary Emulsion—Optional silicone gel/elastomer/paste+$H_2O$+other active ingredients+shear→primary emulsion $W_1/O$ Step 5: Preparation of Multiple Emulsion $W_1/O/W_2$—Optional
   $W_1/O+H_2O$+shear→$W_1/O/W_2$ Multiple Emulsion In Step 1, the molar ratio of the mono-alkenyl polyether to the ≡SiH in the ≡SiH siloxane should be between 0.9:1 to 1:100.

The weight ratio of the active ingredient to the weight of the ≡SiH siloxane with polyether groups and the α,ω-unsaturated hydrocarbon can be from 1:98 to 2:1, but preferably is between 1:15 to 1:5. The weight ratio of the "oil" to the weight of the ≡SiH siloxane with polyether groups and the α,ω-unsaturated hydrocarbon can be from 1:1 to 98:1, but preferably is between 5:1 to 15:1. The ratio of the ≡SiH in the ≡SiH containing siloxane with polyether groups and the α,ω-unsaturated hydrocarbon can be from 2:1 to 1:2, but preferably is 1:1.

In optional Step 3, the silicone paste may contain 60–98 percent by weight of the active ingredient and/or the oil. In Steps 4 and 5, the weight ratio of water to the silicone paste can be 95:5 to 5:95.

If desired, post cure caused by residual crosslinking hydrosilylation reactions occurring in silicone elastomers can be terminated by introducing an ≡SiH quenching agent such as a vinylsiloxane or a vinylsilane. While vinylsiloxanes and/or vinylsilanes can be used to completely terminate post cure, vinylsiloxanes are preferred to react with ≡SiH over other types of alkenylsiloxanes. In the process of making compositions according to the present invention, a vinylsiloxane can be introduced at the shear & swell Step 3. When this is carried out, any on-going reactions of residual functionalities will be shifted to reactions between the incoming vinylsiloxane and the residual ≡SiH, with the result that crosslinking reactions will be terminated.

Representative of some organosilicon compounds and polymers which can be used as quenching agents are silanes such as vinyl-t-butyldimethylsilane, vinyldiethylmethylsilane, vinylethyldimethylsilane, vinyltriethylsilane, vinyltrimethylsilane, divinyldimethylsilane, and divinyltetramethyldisilane; and siloxanes such as vinylpentamethyldisiloxane, 1,3-divinyltetramethyldisiloxane, a vinyltrisiloxane such as $(CH_3)_3SiOSi(CH=CH_2)(CH_3)OSi(CH_3)_3$, 1,5-divinylhexamethyltrisiloxane, and a divinylsiloxane oligomer having an average structure $(CH_2=CH)Me_2SiO(Me_2SiO)_8SiMe_2(CH=CH_2)$ where Me represents the methyl group.

Other types of quenching agents can also be used such as strong platinum complexing ligands, terminal alkynes, and amino acid esters. Representative ligands include trialkyl and triaryl phosphines such as triphenylphosphine $PPh_3$; amines, diamines, and triamines such as n-butylamine $CH_3(CH_2)_3NH_2$, triethanolamine $(HOCH_2CH_2)_3N$, and tetramethylethylene diamine $(CH_3)_2NCH_2CH_2N(CH_3)_2$; and organic sulfides such as ethyl phenyl sulfide $C_6H_5SC_2H_5$.

Some examples of suitable terminal alkynes which can be used are acetylene, propyne, 1-butyne, 1-pentyne, 4,4-dimethyl-1-pentyne, 1-hexyne, 5-methyl-1-hexyne, and 1-decyne.

In addition, the quenching agent can be an amino acid ester, preferably a sulfur containing amino acid ester, such as methionine methyl ester, methionine ethyl ester, cysteine methyl ester, cysteine ethyl ester, and cystine dimethyl ester.

The feature of using quenching agents to terminate post cure is the subject matter of copending application U.S. Ser. No. 08/964,546, filed Nov. 5, 1997, now U.S. Pat. No. 5,929,164, in the name of Shizhong Zhang, entitled "Quenching Post Cure"; and copending application U.S. Ser. No. 08/964,547, filed Nov. 5, 1997, now U.S. Pat. No. 5,977,280, in the name of Donald A. Kadlec, William J. Schulz, and Shizhong Zhang, entitled "Terminating Post Cure With Amino Acid Esters". Both applications are assigned to the same assignee as the present invention.

The ≡Si—H siloxane in Step 1 is represented by compounds of the formula $R_3SiO(R'_2SiO)_a(R''HSiO)_bSiR3$, compounds of the formula $HR_2SiO(R'_2SiO)_cSiR_2H$, or compounds of the formula $HR_2SiO(R'_2SiO)_a(R''HSiO)_bSiR_2H$. Mixtures of these types of compounds can also be employed. In the three formulas, R, R', and R'', are alkyl groups with 1–6 carbon atoms; a is 0–250; b is 1–250; and c is 0–250.

The ≡Si—H containing polysiloxane can also comprise an alkylhydrogen cyclosiloxane or an alkylhydrogen dialkyl cyclosiloxane copolymer, represented in general by the formula $(R'_2SiO)_{a'}(R''HSiO)_{b'}$, where R' and R'' are as defined above, and where a' is 0–7 and b' is 3–10. Some representative compounds of these types are $(OSiMeH)_4$, $(OSiMeH)_3(OSiMeC_6H_{13})$, $(OSiMeH)_2(OSiMeC_6H_{13})_2$, and $(OSiMeH)(OSiMeC_6H_{13})_3$, where Me represents —$CH_3$.

An α,ω-unsaturated hydrocarbon is used in Step 2, and the most preferred α,ω-unsaturated hydrocarbon is an α,ω-diene of the formula $CH_2=CH(CH_2)_dCH=CH_2$ where d is 0–20. Some representative examples of suitable α,ω-dienes for use herein are 1,3-butadiene; 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

However, other α,ω-unsaturated hydrocarbons can be used such as α,ω-diynes of the formula $CH≡C(CH_2)_eC≡CH$; or α,ω-ene-ynes of the formula $CH_2=CH(CH_2)_eC≡CH$ where e is 0–20. Some representative examples of suitable α,ω-diynes for use herein are 1,3-butadiyne $HC≡C—C≡CH$ and 1,5-hexadiyne (dipropargyl) $HC≡C—CH_2CH_2—C≡CH$. One example of a suitable α,ω-ene-yne for use herein is hexene-5-yne-1 $CH_2=CHCH_2CH_2C≡CH$.

The process in Steps 1 and 2 requires a catalyst to effect the reaction between the ≡SiH containing siloxane, the mono-alkenyl polyether, and the α,ω-unsaturated hydrocarbon. Suitable catalysts are Group VIII transition metals, i.e., the noble metals. Such noble metal catalysts are described in U.S. Pat. No. 3,923,705, incorporated herein by reference. A particularly preferred catalyst is Karstedt's catalyst described in U.S. Pat. Nos. 3,715,334 and 3,814,730, incorporated herein by reference. Karstedt's catalyst is a platinum divinyl tetramethyl disiloxane complex, typically containing about one weight percent of platinum, carried in a polydimethylsiloxane fluid or in a solvent such as toluene.

The particular catalyst used in the examples was Karstedt's catalyst as a one weight percent of platinum carried in a 2.0 $mm^2$/s polydimethylsiloxane fluid. Another preferred platinum catalyst is a reaction product of chloroplatinic acid and an organosilicon compound containing terminal aliphatic unsaturation. It is described in U.S. Pat. No. 3,419,593, incorporated herein by reference.

The mono-alkenyl polyether is a compound of the formula $CH_2=CH(CH_2)_fO(CH_2CH_2O)_g(CH_2CH_3CHO)_hT$, or a compound of the formula $CH_2=CH-Q-O(CH_2CH_2)_g$ $(CH_2CH_3CHO)_hT$. In the formulas, T represents an end group which can be hydrogen; a C1–C10 alkyl group such as methyl, ethyl, propyl, butyl, and decyl; an aryl group such as phenyl; or a C1–C20 acyl group such as acetyl, propionyl, butyryl, lauroyl, myristoyl, and stearoyl. Q is a divalent linking group containing unsaturation such as phenylene —$C_6H_4$—. The value of f is 0–6; g has a value of 4–100; and h can be zero or have a value of 1–100.

The term oil as used herein is intended to include compounds containing a silicon atom such as low molecular weight linear and cyclic volatile and non-volatile alkyl and aryl siloxanes, and low molecular weight functional linear and cyclic siloxanes. Most preferred, however, are low molecular weight linear and cyclic volatile methyl siloxanes. Thus, this particular component constitutes what is shown as the "oil" in Step 2 of the process illustrated above.

Linear volatile methyl siloxanes have the formula $(CH_3)_3SiO\{(CH_3)_2SiO\}_kSi(CH_3)_3$. The value of k is 0–5. Cyclic volatile methyl siloxanes have the formula $\{(CH_3)_2SiO\}_m$. The value of m is 3–9. Preferably, these volatile methyl siloxane have a boiling point less than about 250° C. and viscosity of about 0.65 to about 5.0 mm²/s.

Representative linear volatile methyl siloxanes are hexamethyldisiloxane (MM) with a boiling point of 100° C., viscosity of 0.65 mm²/s, and formula $Me_3SiOSiMe_3$; octamethyltrisiloxane (MDM) with a boiling point of 152° C., viscosity of 1.04 mm²/s, and formula $Me_3SiOMe_2SiOSiMe_3$; decamethyltetrasiloxane (MD$_2$M) with a boiling point of 194° C., viscosity of 1.53 mm²/s, and formula $Me_3SiO(Me_2SiO)_2SiMe_3$; dodecamethylpentasiloxane (MD$_3$M) with a boiling point of 229° C., viscosity of 2.06 mm²/s, and formula $Me_3SiO(Me_2SiO)_3SiMe_3$; tetradecamethylhexasiloxane (MD$_4$M) with a boiling point of 245° C., viscosity of 2.63 m and formula $Me_3SiO(Me_2SiO)_4SiMe_3$; and hexadecamethylheptasiloxane (MD$_5$M) with a boiling point of 270° C., viscosity of 3.24 mm²/s, and formula $Me_3SiO(Me_2SiO)_5SiMe_3$.

Representative cyclic volatile methyl siloxanes are hexamethylcyclotrisiloxane (D$_3$) a solid with a boiling point of 134° C. and formula $\{(Me_2)SiO\}_3$; octamethylcyclotetrasiloxane (D$_4$) with a boiling point of 176° C., viscosity of 2.3 mm²/s, and formula $\{(Me_2)SiO\}_4$; decamethylcyclopentasiloxane (D$_5$) with a boiling point of 210° C., viscosity of 3.87 mm²/s, and formula $\{(Me_2)SiO\}_5$; and dodecamethylcyclohexasiloxane (D$_6$) with a boiling point of 245° C., viscosity of 6.62 mm²/s, and formula $\{(Me_2)SiO\}_6$.

In these formulas, M and D represent the monofunctional "M" units $(CH_3)_3SiO_{1/2}$ and the difunctional "D" units $(CH_3)_2SiO_{2/2}$, respectively.

The invention also includes using low molecular weight linear and cyclic non-volatile alkyl and aryl siloxanes represented respectively by the formulas $R^a{}_3SiO(R^a{}_2SiO)_nSiR^a{}_3$ and $(R^a{}_2SiO)_p$. $R^a$ can be an alkyl group with 1–20 carbon atoms, or an aryl group such as phenyl. The value of n is 0–80, preferably 5–20. The value of p is 3–9, preferably 4–6. These polysiloxanes generally have a viscosity in the range of about 5–100 mm²/s.

Polysiloxanes can also be used where n has a value sufficient to provide siloxane polymers with a viscosity in the range of about 100–1,000 mm²/sec. Typically, n can be about 80–375. Illustrative polysiloxanes are polydimethylsiloxane, polydiethylsiloxane, polymethylethylsiloxane, polymethylphenylsiloxane, and polydiphenylsiloxane.

Low molecular weight functional polysiloxanes can also be employed, and are represented by the formula $R^b{}_3SiO(R^bYSiO)_nSiR^b{}_3$ where $R^b$ can be alkyl groups with 1–20 carbon atoms or aryl groups such as phenyl, Y is a functional group, and n is 0–80. Examples of such functional polysiloxanes containing functional groups represented by Y are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

The invention is not limited to using only low molecular weight siloxanes. Other types of oils can be used in Step 2 of the process. Thus, an oil or mixture of oils may be used.

The term oil is therefore further intended to include (i) organic compounds, (ii) compounds containing a silicon atom as enumerated above, (iii) mixtures of organic compounds, (iv) mixtures of compounds containing a silicon atom, or (v) mixtures of organic compounds and compounds containing a silicon atom; used to dissolve, suspend, or change the physical properties of other materials.

In general, the organic compounds used as oils are aromatic hydrocarbons, aliphatic hydrocarbons, alcohols, aldehydes, ketones, amines, esters, ethers, glycols, glycol ethers, alkyl halides, or aromatic halides. Representative compounds are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Maker's & Painter's (VM&P) solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, benzyl acetate, and isopropyl palmitate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as petroleum jelly, mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Other miscellaneous organic oils can also be used such as acetonitrile, nitromethane, dimethylformamide, propylene oxide, trioctyl phosphate, butyrolactone, furfural, pine oil, turpentine, and m-cresol.

Further intended to be included in the term oil are volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, the term oil is intended to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

As noted above, the term "oil" is not considered synonymous with the phrase active ingredient, and the phrase active ingredient is not considered synonymous with the term "oil", within the context of the invention.

As used herein, the phrases active ingredient and active drug ingredient are intended generally to have the meanings used and defined by the United States Department of Health & Human Services Food and Drug Administration, contained in Title 21, Chapter I, of the Code of Federal Regulations, Parts 200–299 and Parts 300–499.

Thus, active ingredient can include any component that is intended to furnish pharmacological activity or other direct effect in the diagnosis, cure, mitigation, treatment, or prevention of disease, or to affect the structure or any function of the body of man or other animals. The phrase can include those components that may undergo chemical change in the manufacture of drug products and be present in drug products in a modified form intended to furnish the specified activity or effect.

As noted in the Code, this excludes ingredients such as a coloring, emulsifier, excipient, flavoring, lubricant, preservative, or solvent.

Some representative examples of active ingredients including drugs, are vitamin-minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Useful active ingredients for use in processes according to the invention include both fat or oil-soluble vitamins as well as water-soluble vitamins. Oil-soluble vitamins useful herein include, but are not limited to, Vitamin $A_1$, RETINOL, $C_2$–$C_{18}$ esters of RETINOL, vitamin E, TOCOPHEROL, esters of vitamin E, and mixtures thereof. RETINOL includes trans-RETINOL, 13-cis-RETINOL, 11-cis-RETINOL, 9-cis-RETINOL, and 3,4-didehydro-RETINOL. The oil-soluble vitamin can be used in Steps 3 and 4 in the composition in an amount of from 0.01 to about 50 percent by weight.

RETINOL, it should be noted, is an International Nomenclature Cosmetic Ingredient Name (INCI) designated by The Cosmetic, Toiletry, and Fragrance Association (CTFA), Washington DC, for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Water-soluble vitamins useful herein include, but are not limited to, Vitamin C, Vitamin $B_1$, Vitamin $B_2$, Vitamin $B_6$, Vitamin $B_{12}$, niacin, folic acid, biotin, and pantothenic acid. Other suitable water-soluble vitamins and the INCI names for the vitamins considered included herein are ASCORBYL DIPALMITATE, ASCORBYL METHYLSILANOL PECTINATE, ASCORBYL PALMITATE, and ASCORBYL STEARATE. The water-soluble vitamin, like the oil-soluble vitamin, can be used in Steps 3 and 4 in the composition in an amount of from 0.01 to about 50 percent by weight.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active ingredient used in processes according to the invention can be a water-soluble or an oil-soluble active drug ingredient. Representative examples of some suitable water-soluble active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole.

Representative examples of some suitable oil-soluble active drug ingredients which can be used are clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The process is carried out by combining the ≡SiH containing siloxane(s), the mono-alkenyl polyether, the active ingredient, the oil, the α,ω-unsaturated hydrocarbon, and the platinum catalyst; and mixing these ingredients at elevated temperature until a gel, elastomer, paste, or emulsion, is formed.

If desired, all of the reactants (i.e., the ≡SiH containing siloxane(s), the mono-alkenyl polyether, the active ingredient, the oil, the α,ω-unsaturated hydrocarbon, and the platinum catalyst), can be combined and reacted in one pot. One pot methods are described generally in U.S. Pat. No. 5,889,108 (Mar. 30, 1999), which is assigned to the same assignee as the present invention.

The gel, elastomer, paste, or emulsion, can also be further modified in Steps 3 and 4 to include additional active ingredients, or it can be diluted with additional oils, to form the final composition.

Thus, additional amounts of an oil can be added to the gel, i.e., Optional Step 3, and the resulting mixture can be subjected to shear force to form the paste. In Step 4, shear force can again be used, during or after which water is added to the paste, to form a primary emulsion $W_1/O$. The application of shear force can then be continued according to Step 5, whereby the primary emulsion $W_1/O$ prepared in Step 4 can be formed into a $W_1/O/W_2$ multiple emulsion.

Any type of mixing or shearing equipment may be used to perform these steps, such as batch mixers, planetary mixers, single or multiple screw extruders, dynamic or static mixers, colloid mills, homogenizers, sonolators, or combinations thereof.

Step 3 of the process is an optional step, as noted above. However, when Step 3 is conducted and an additional oil is to be included, the additional oil should be an oil in which the "active ingredient" is soluble. This is particularly important where the active ingredient is a vitamin. Some suitable oils include silicone and hydrocarbon based oils. In addition, the additional oil should satisfy the melting point and the solubility requirements necessary for end uses being contemplated.

Typically, the process is carried out using approximately a 1:1 equivalent ratio of the $\equiv$Si—H in the $\equiv$Si—H containing siloxane with polyether groups and the $\alpha,\omega$-unsaturated hydrocarbon. It is expected that useful materials may also be prepared by carrying out the process with an excess of either the $\equiv$Si—H containing siloxane with polyether groups or the $\alpha,\omega$-unsaturated hydrocarbon, but this would be considered a less efficient use of the materials. The remainder of the composition comprises the active ingredient and the oil, in amounts generally within the range of about 60–98 percent by weight of the composition.

Step 3 may require (i) using an additional oil to solubilize the active ingredient especially in the case of a vitamin(s), by adding the vitamin(s) to the additional oil at room temperature while mixing; and (ii) adding the additional oil containing the vitamin(s) slowly to the elastomeric silicone polyether at room temperature while mixing.

In Steps 4 and 5, a multiple emulsion $W_1/O/W_2$ which is capable of housing fat and water-soluble active ingredients side by side in the inner phases of the emulsion, can be prepared by (i) first producing an inner emulsion, i.e., a primary emulsion $W_1/O$, and (ii) then adding the inner or primary emulsion $W_1/O$ to the outer aqueous phase $W_2$ using a minimum amount of mixing energy.

In forming primary emulsion $W_1/O$, it is preferred to use 0.1 to 99 percent by weight of the aqueous phase $W_1$, which amount includes the weight of any water-soluble active ingredient such as a vitamin(s), which may be carried therein. The oil phase O of primary emulsion $W^1/O$ is used in an amount of about 1 to 99.9 percent by weight, which amount includes the weight of the elastomeric silicone polyether, any other oil, oil-soluble vitamin(s), or fat-soluble active ingredient included therein.

A multiple emulsion $W_1/O/W_2$ can then be prepared by simply mixing together about 0.1 to 70 percent by weight of the primary emulsion $W_1/O$, with about 30 to 99.9 percent by weight of the aqueous final continuous phase $W_2$, which latter amount includes the weight of any other water-soluble active ingredients contained in the final continuous phase.

EXAMPLES

The following examples are set forth in order to illustrate this invention in more detail.

Example 1

Process for Making Elastomeric Silicone Polyethers

In this example, an ESCO EL-1 processor mixer was employed. The processor mixer was equipped with a one liter jacketed glass container having heating and cooling capability, an anchor sweep blade with speed control settings of 20–300 rpm (2–31 rad/s), a high speed homogenizer with Cowles type blades, speed controls for 750–15,000 rpm (78–1,570 rad/s) operation, a temperature gauge, a product inlet, a vacuum connection, and a circulation bath with heating and cooling capacity. The starting materials 1(a), 1(b), and 2–7, used in preparing elastomeric silicone polyethers according to this first Example 1 are shown below, and the resulting elastomeric silicone polyethers prepared in this example were used in the following Examples 2–10.

Starting Materials Used in Example 1:

1(a). The $\equiv$SiH siloxane used in the preparation of elastomeric silicone polyethers according to Examples 2–8 was a copolymer generally corresponding to the formula $Me_3SiO(Me_2SiO)_{93}(MeHSiO)_6SiMe_3$ in which Me represents methyl. This copolymer has a degree of polymerization (DP) of 101. It should be noted that in this copolymer, there are six (6) reactive sites available for reaction or crosslinking. Only a fraction of the reactive sites are consumed in the reaction with the mono-alkenyl polyether, however. After the initial reaction, and after having been exposed to the active ingredient, the remaining reactive sites are consumed in crosslinking with the $\alpha,\omega$-unsaturated hydrocarbon. This is shown in Table 1, in the fourth column entitled "SiH:PE Ratio". These are the ratio of the units of $\equiv$SiH in the $\equiv$Si—H containing polysiloxane, versus the mols of $EO_4$ or the mols of $EO_7$ which is contained in the final composition. In the case of Examples 2–8, the ratio remained constant and was equal to 12:1. Stated in other words, the elastomeric silicone polyether had a 12:1 ratio of crosslinks:$EO_4$ or $EO_7$, whichever is the case.

1(b). The $\equiv$SiH siloxane used in the preparation of elastomeric silicone polyethers according to Examples 9 and 10 was a copolymer generally corresponding to the formula $Me_3SiO(Me_2SiO)_{77}(MeHSiO)_{20}SiMe_3$ in which Me represents methyl. This copolymer has a molecular weight of about 7,067; and its degree of polymerization (DP) is 99. It is noted that in this copolymer, there are twenty (20) reactive sites available for reaction or crosslinking. Only a fraction of the reactive sites are consumed in the reaction with the mono-alkenyl polyether, however. After the initial reaction, and after having been exposed to the active ingredient, the remaining reactive sites are consumed in crosslinking with the $\alpha,\omega$-unsaturated hydrocarbon. This is shown in Table 1, in the fourth column entitled "SiH:PE Ratio". These are the ratio of the units of $\equiv$SiH in the $\equiv$Si—H containing polysiloxane, versus the mols of $EO_7$ or the mols of $EO_{12}$ which is contained in the final composition. In the case of Examples 9 and 10, the ratios were equal to 20:1 and 10:1, respectively. Stated in other words, the elastomeric silicone polyether had either a 20:1 or a 10:1 ratio of crosslinks:$EO_7$ or $EO_{12}$, whichever is the case.

2. The $\alpha,\omega$-unsaturated hydrocarbon was 1,5-hexadiene.

3. The mono-alkenyl polyethers had chain lengths of 4, 7, and 12, and were compositions corresponding to the general formulas $CH_2=CH(CH_2)O(CH_2CH_2O)_4H$, $CH_2=CH(CH_2)O(CH_2CH_2O)_7H$, and $CH_2=CH(CH_2)O(CH_2CH_2O)_{12}H$, respectively.

4. The oil consisted of the cyclic siloxane species decamethylcyclopentasiloxane.

5. The catalyst was a platinum divinyltetramethyldisiloxane complex containing about one weight percent of platinum carried in a solvent, i.e., Karstedt's catalyst.

6. The post cure quenching agent was a dimethylvinylsiloxy terminated disiloxane of the formula $(CH_3)_2H_2C=CHSiOSiCH=CH_2(CH_3)_2$.

7. The active ingredients were vitamin E; an antimicrobial agent 5-chloro-2-(2,4-dichlorophenoxy)phenol, i.e., TRICLOSAN, which is shown below; a sunburn prevention agent 2-ethylhexyl methoxy cinnamate, i.e., OCTYL-METHOXY CINNAMATE; two astringents (i) aluminum chlorohydrate and (ii) aluminum zirconium tetrachlorohydrex glycine complex, i.e., ALUMINUM ZIRCONIUM TETRACHLOROHYDREX GLY or AZG; and estradiol, a female sex hormone, which is also shown below.

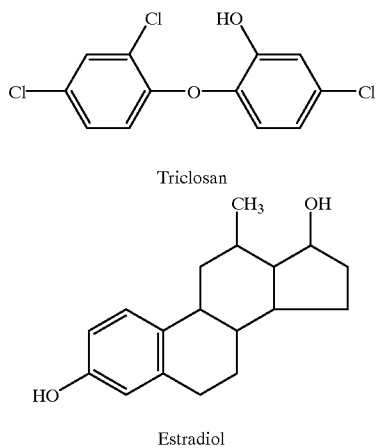

Triclosan

Estradiol

An elastomeric silicone polyether was prepared by adding to the ESCO EL-1 processor mixer, the ≡SiH siloxane, the mono-alkenyl polyether, and 84–95 percent by weight of the total amount of $D_5$ used in the example. After loading the materials into the mixer container, the mixer was closed. Heating of the mixer was initiated by setting the circulatory bath set point to about 70° C. The speed of the sweep blade of the mixer was activated to about 15–30 percent of its full capacity, and the speed of the homogenizer of the mixer was activated to about 5 percent of its full capacity. The platinum catalyst was added to the mixer via a syringe inserted through the port hole of the mixer, and the timer was started. Mixing was continued for about 30 minutes. The active ingredient was then added, and mixing of the contents in the container was continued for a minimum of another 15 minutes. Using an analytical balance, the α,ω-unsaturated hydrocarbon, i.e., 1,5-hexadiene, was weighed into a one ounce vial along with 10–20 g of decamethylcyclopentasiloxane, and the vial was capped. The remaining portion, i.e., 5–16 percent by weight, of decamethylcyclopentasiloxane was weighed and placed in a beaker.

Because of the volatility characteristics of 1,5-hexadiene, care was taken when adding it to the reaction mixture. The homogenizer was turned off, and the speed of the scraper was reduced to about 5 percent of its full capacity. The inlet plug of the ESCO processor mixer was removed, and a funnel with an extended stem, was inserted into the port hole of the inlet, so that the stem reached below the surface of the liquid in the container. The α,ω-unsaturated hydrocarbon, i.e., 1,5-hexadiene, was mixed with a portion of decamethylcyclopentasiloxane, and poured into the funnel, followed by the addition of the remaining portion of decamethylcyclopentasiloxane. When the contents in the funnel had been added, the funnel was removed, the inlet was closed, and the timer was restarted.

The speed of the scraper blade was increased to 15–30 percent of its full capacity, and the speed of the homogenizer was increased to 5–10 percent of its full capacity. The fluid in the mixer container began forming a gel, evidenced by material in the container thickening and climbing up the shaft of the mixer. The time of this occurrence of gelation was noted in a log book, and mixing of the contents was continued. The total time of mixing measured from the point of addition of the α,ω-unsaturated hydrocarbon was a minimum of 3 hours at a constant temperature of about 70° C. At the end of this time, the set point of the mixer circulatory bath was lowered to 25° C., and mixing was continued. The post cure quenching agent was added, followed by dilution of the contents of the mixer container with decamethylcyclopentasiloxane.

Examples 2–10

Using the above procedure, nine (9) elastomeric silicone polyethers containing six (6) different types of an active ingredient were prepared, and the characteristics of the nine elastomeric silicone polyethers prepared according to Examples 2–10 are shown in Table 1.

TABLE 1

| Active Ingredient | Weight % Elastomer in Gel | EO Chain Length | SiH:PE Ratio | Weight % Active in Elastomer | % Active After Dilution With D5 | Ex. No. |
|---|---|---|---|---|---|---|
| Vitamin E | 15 | 4 | 12:1 | 8.33 | 5 | 2 |
| Vitamin E | 15 | 7 | 12:1 | 0.87 | 0.87 | 3 |
| Triclosan | 15 | 4 | 12:1 | 0.33 | 0.20 | 4 |
| Octyl-methoxy Cinnamate | 15 | 4 | 12:1 | 16.70 | 10 | 5 |
| Aluminum Chlorohydrate | 15 | 4 | 12:1 | 25 | 25 | 6 |
| AZG | 15 | 7 | 12:1 | 15 | 15 | 7 |
| Estradiol | 15 | 7 | 12:1 | 0.75 | 0.53 | 8 |
| Estradiol | 15 | 12 | 20:1 | 5 | 5 | 9 |
| Estradiol | 20 | 7 | 10:1 | 5.13 | 5 | 10 |

In the Table, in Examples 2–10, it is noted that $D_5$ constituted the component making up the balance of the gel composition prepared in each of these examples. Thus, in Example 2, the gel composition comprised 15 percent by weight of the elastomeric silicone polyether, about 8.3 percent by weight of the active ingredient vitamin E, and the balance of the gel composition to 100 percent was decamethylcyclopentasiloxane.

It should be pointed out that other types of reactive compositions can be used in preparing elastomeric silicone polyethers herein without departing from the spirit of the invention.

For example, one can prepare elastomeric silicone polyethers by reacting the mono-alkenyl polyether with the following other types of reactive compositions, instead of using the particular ≡Si—H containing polysiloxanes and α,ω-unsaturated hydrocarbons enumerated above:

ZMe$_2$SiO(Me$_2$SiO)$_r$(MeHSiO)$_s$SiMe$_2$Z and
QMe$_2$SiO(Me$_2$SiO)$_t$(MeQSiO)$_u$SiMe$_2$Q
where Me is methyl; Z is CH$_3$ or H provided there are at least two H atoms per molecule; Q is vinyl or another alpha-unsaturated alkenyl group or CH$_3$ provided there are at least two carbon-carbon double bonds per molecule; r is 0–1,000; s is 0–100; t is 0–1,000; and u is 0–100.

One can also prepare elastomeric silicone polyethers by reacting the mono-alkenyl polyether with the following types of reactive compositions, instead of using the particular ≡Si—H containing polysiloxanes and α,ω-unsaturated hydrocarbons enumerated above:

$(RMe_2SiO_{1/2})_v(SiO_{4/2})_w(RSiO_{3/2})_x(RMeSiO_{2/2})_y$ and $QMe_2SiO(Me_2SiO)_z(MeQSiO)_\lambda SiMe_2Q$
where Me is methyl; R is methyl or H provided there are at least two H atoms per molecule; Q is vinyl or another alpha-unsaturated alkenyl group or methyl provided there are at least two carbon-carbon double bonds per molecule; v is 2–50; w is 0–20; x is 0–50; y is 0–1,000; z is 0–1,000; and $\lambda$ is 0–100.

Crosslinked three-dimensional gelled networks of elastomeric silicones containing an active ingredient and an oil, according to this invention, can also be prepared by using the silicone elastomer described in U.S. Pat. No. 5,654,362 (Aug. 5, 1997); the silicone elastomer described in U.S. Pat. No. 5,880,210 (Mar. 9, 1999); or the silicone elastomer described in U.S. patent application Ser. No. 09/299,864, filed Apr. 28, 1999, entitled "Elastomeric Silicone Terpolymer".

The silicone elastomer in U.S. Pat. No. 5,654,362 is similar to the elastomeric silicone polyether preferred herein, but it does not contain polyether groups. It is prepared by combining an ≡Si—H containing polysiloxane, an α,ω-unsaturated hydrocarbon, a platinum catalyst, and an oil.

The silicone elastomer in U.S. Pat. No. 5,880,210 is similar to the elastomeric silicone polyether preferred herein, but it contains long chain alkyl groups instead of polyether groups. It is prepared by combining an ≡Si—H containing polysiloxane, an α-olefin containing 3–40 carbon atoms, an α,ω-unsaturated hydrocarbon, a platinum catalyst, and an oil. Representative α-olefins are propylene, 1-pentene, 1-decene ($C_{10}$), 1-undecene, 1-dodecene, 1-tridecene, 1-tetradecene, 1-pentadecene ($C_{15}$), 1-hexadecene, 1-octadecene, 1-nonadecene, 1-eicosene ($C_{20}$), 1-heptacosene, and α-olefin fractions containing various amounts of $C_{22-C30+}$ α-olefins sold under the trademark GULFTENE® 24–28 and GULFTENE® 30+ by the Chevron Chemical Company, Houston, Tex.

The silicone elastomer in U.S. patent application Ser. No. 09/299,864 is similar to the elastomeric silicone polyether preferred herein, but it contains long chain alkyl groups in addition to polyether groups. It is prepared by combining an ≡Si—H containing polysiloxane, a mono-alkenyl polyether, an α-olefin containing 10–40 carbon atoms, an α,ω-unsaturated hydrocarbon, a platinum catalyst, and an oil. Representative α-olefins are shown above.

The compositions according to this invention have particular value in the personal care arena. They can be used alone, or blended with other cosmetic ingredients, to form a variety of personal care products.

Thus, they are useful as carriers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, and provide conditioning benefits.

In cosmetics, they can function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, the compositions can impart a dry, silky-smooth, payout.

In addition, the compositions exhibit other advantageous and beneficial properties such as shelf stability and ease of preparation. Hence, they can have wide application, but especially in antiperspirants, deodorants, skin care products, and for conditioning hair.

Further, the compositions have utility as additives for cellulosic or synthetic nonwoven carrier substrates used in wet-like cleansing wipes such as wet-wipes, tissues, and towels, marketed generally for personal hygiene and household cleaning tasks.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising an elastomeric silicone polyether prepared by a method comprising combining and reacting:

(A) an ≡Si—H containing polysiloxane of the formula $R_3SiO(R'_2SiO)_a(R"HSiO)_bSiR_3$, the formula $(R'_2SiO)_{a'}(R"HSiO)_{b'}$, the formula $HR_2SiO(R'_2SiO)_cSiR_2H$, or the formula $HR_2SiO(R'_2SiO)_a(R"HSiO)_bSiR_2H$, where R, R', and R" are alkyl groups with 1–6 carbon atoms, a is 0–250, a' is 0–7, b is 1–250, b' is 3–10, and c is 0–250;

(B) a mono-alkenyl polyether of the formula $CH_2=CH(CH_2)_fO(CH_2CH_2O)_g(CH_2CH_3CHO)_hT$, or the formula $CH_2=CH—Q—O(CH_2CH_2O)_g(CH_2CH_3CHO)_hT$, where T is hydrogen, a $C_1$–$C_{10}$ alkyl group, an aryl group, or a $C_1$–$C_{20}$ acyl group; Q is a divalent linking group containing unsaturation; f is 0–6, g is 4–100; and h is zero or 1–100;

(C) an active ingredient capable of furnishing pharmacological activity or other direct effect in diagnosis, cure, mitigation, treatment, or prevention of disease, or which affects structures or functions of the body of man or other animal, including components that undergo chemical change in the manufacture of drug products or are present in drug products in a modified form intended to furnish specified activities or effects;

(D) an α,ω-unsaturated hydrocarbon selected from the group consisting of α,ω-dienes of the formula $CH_2=CH(CH_2)_dCH=CH_2$, α,ω-diynes of the formula $CH\equiv C(CH_2)_eC\equiv CH$, and α,ω-ene-ynes of the formula $CH_2=CH(CH_2)_eC\equiv CH$, where d is 0–20 and e is 0–20; and (E) a platinum catalyst; in the presence of (F) an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom;

and allowing the reaction to continue until there is formed a crosslinked three-dimensional gelled network of an elastomeric silicone polyether containing the active ingredient and the oil.

2. A composition according to claim 1 in which the oil is a linear volatile methyl siloxane of the formula $(CH_3)_3SiO\{(CH_3)_2SiO\}_kSi(CH_3)_3$ where k is 0–5, or a cyclic volatile methyl siloxane of the formula $\{(CH_3)_2SiO\}_m$ where m is 3–8, the volatile methyl siloxane have a boiling point less than about 250° C. and a viscosity of 0.65–5.0 $mm^2/s$.

3. A composition according to claim 1 in which the active ingredient is an oil-soluble active ingredient.

4. A composition according to claim 1 in which the active ingredient is a water-soluble active ingredient.

5. An emulsion containing the composition according to claim 4.

6. An emulsion containing the composition according to claim 4.

7. A multiple emulsion containing the composition according to claim 3.

8. A multiple emulsion containing the composition according to claim 4.

9. A method of treating hair, skin, or underarm comprising applying to the hair, skin, or underarm, the composition according to claim 1.

10. A composition comprising an elastomeric silicone polyether prepared by a method comprising combining and reacting:

(A) an $\equiv$Si—H containing polysiloxane of the formula $R_3SiO(R'_2SiO)_a(R''HSiO)_bSiR_3$, the formula $(R'_2SiO)_{a'}(R''HSiO)_{b'}$, the formula $HR_2SiO(R'_2SiO)_cSiR_2H$, or the formula $HR_2SiO(R'_2SiO)_a(R''HSiO)_bSiR_2H$, where R, R', and R" are alkyl groups with 1–6 carbon atoms, a is 0–250, a' is 0–7, b is 1–250, b' is 3–10, and c is 0–250;

(B) a mono-alkenyl polyether of the formula $CH_2=CH(CH_2)_fO(CH_2CH_2O)_g(CH_2CH_3CHO)_hT$, or the formula $CH_2=CH-Q-O(CH_2CH_2O)_g(CH_2CH_3CHO)_hT$, where T is hydrogen, a $C_1-C_{10}$ alkyl group, an aryl group, or a $C_1-C_{20}$ acyl group; Q is a divalent linking group containing unsaturation; f is 0–6, g is 4–100; and h is zero or 1–100;

(C) an active ingredient selected from the group consisting of vitamins, antimicrobial agents, sunburn prevention agents, astringents, and hormones;

(D) an $\alpha,\omega$-unsaturated hydrocarbon selected from the group consisting of $\alpha,\omega$-dienes of the formula $CH_2=CH(CH_2)_dCH=CH_2$, $\alpha,\omega$-diynes of the formula $CH\equiv C(CH_2)_eC\equiv CH$, and $\alpha,\omega$-ene-ynes of the formula $CH_2=CH(CH_2)_eC\equiv$, where d is 0–20 and e is 0–20; and (E) a platinum catalyst; in the presence of (F) an oil selected from the group consisting of (i) organic compounds, (ii) compounds containing a silicon atom, (iii) mixtures of compounds, (iv) mixtures of compounds containing a silicon atom, and (v) mixtures of organic compounds and atom; compounds containing a silicon atom;

and allowing the reaction to continue until there is formed a crosslinked three-dimensional gelled network of an elastomeric silicone polyether containing the active ingredient and the oil.

11. A composition comprising an elastomeric silicone prepared by a method comprising combining and reacting:

(A) an $\equiv$Si—H containing polysiloxane of the formula $R_3SiO(R'_2SiO)_a(R''HSiO)_bSiR_3$, the formula $(R'_2SiO)_{a'}(R''HSiO)_{b'}$, the formula $HR_2SiO(R'_2SiO)_cSiR_2H$, or the formula $HR_2SiO(R'_2SiO)_a(R''HSiO)_bSiR_2H$, where R, R', and R" are alkyl groups with 1–6 carbon atoms, a is 0–250, a' is 0–7, b is 1–250, b' is 3–10, and c is 0–250;

(B) optionally, a mono-alkenyl polyether, an $\alpha$-olefin, or a mono-alkenyl polyether and an $\alpha$-olefin;

(C) an active ingredient selected from the group consisting of vitamins, antimicrobial agents, sunburn prevention agents, astringents, and hormones;

(D) an $\alpha,\omega$-unsaturated hydrocarbon selected from the group consisting of $\alpha,\omega$-dienes of the formula $CH_2=CH(CH_2)_dCH=CH_2$, $\alpha,\omega$-diynes of the formula $CH\equiv C(CH_2)_eC\equiv CH$, and $\alpha,\omega$-ene-ynes of the formula $CH_2=CD(CH_2)_eC\equiv CH$, where d is 0–20 and e is 0–20; and (E) a platinum catalyst; in the presence of (F) an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom;

and allowing the reaction to continue until there is formed a crosslinked three-dimensional gelled network of an elastomeric silicone containing the active ingredient and the oil.

\* \* \* \* \*